United States Patent [19]
Burke et al.

[11] Patent Number: 5,305,363
[45] Date of Patent: Apr. 19, 1994

[54] COMPUTERIZED TOMOGRAPHIC SCANNER HAVING A TOROIDAL X-RAY TUBE WITH A STATIONARY ANNULAR ANODE AND A ROTATING CATHODE ASSEMBLY

[75] Inventors: James E. Burke, Villa Park; Lester Miller, Forest Park, both of Ill.; Rodney A. Mattson, Mentor, Ohio; Carl J. Brunnett, Willoughby Hills, Ohio; Theodore A. Resnick, Beachwood, Ohio

[73] Assignee: Picker International, Inc., Highland Hts., Ohio

[21] Appl. No.: 863,182

[22] Filed: Apr. 3, 1992

Related U.S. Application Data

[63] Continuation-in-part of Ser. No. 817,294, Jan. 6, 1992, Pat. No. 5,241,577, and a continuation-in-part of Ser. No. 817,295, Jan. 6, 1992, Pat. No. 5,200,985, and a continuation-in-part of Ser. No. 817,296, Jan. 6, 1992, abandoned.

[51] Int. Cl.$^5$ ............................................. H01J 35/06
[52] U.S. Cl. ..................................... 378/4; 378/134; 378/121; 378/136
[58] Field of Search ............... 378/4, 10, 9, 11, 19, 378/62, 121, 124, 137, 143, 147, 26, 15, 136, 134, 135

[56] References Cited

U.S. PATENT DOCUMENTS

| | | | |
|---|---|---|---|
| 4,122,346 | 10/1978 | Enge | 250/398 |
| 4,135,095 | 1/1979 | Watanabe | 250/445 |
| 4,203,036 | 5/1980 | Tschunt | 250/445 |
| 4,227,088 | 10/1980 | Maydan et al. | 250/445 |
| 4,274,005 | 6/1981 | Yamamura et al. | 250/445 |
| 4,300,051 | 11/1981 | Little | 378/10 |
| 4,368,535 | 1/1983 | Baumann | 378/15 |
| 4,417,171 | 11/1983 | Schmitmann | 313/16 |
| 4,821,305 | 4/1989 | Anderson | 378/136 |
| 4,866,745 | 9/1989 | Akai | 378/9 |
| 4,942,597 | 7/1990 | Van Acker et al. | 378/4 |
| 5,125,012 | 6/1992 | Schittenhelm | 378/10 |
| 5,179,583 | 1/1993 | Oikawa | 378/135 |
| 5,191,600 | 3/1993 | Vincent et al. | 378/10 |
| 5,200,985 | 4/1993 | Miller | 378/135 |
| 5,241,577 | 8/1993 | Burke et al. | 378/135 |

FOREIGN PATENT DOCUMENTS

| | | |
|---|---|---|
| 0377534A1 | 7/1990 | European Pat. Off. |
| 455177A | 4/1991 | European Pat. Off. |
| 456114A | 4/1991 | European Pat. Off. |
| 3226950A | 1/1990 | Japan |
| 1635090A | 4/1990 | U.S.S.R. |

OTHER PUBLICATIONS

Brushless DC Motors and Servo Amplifiers ©1988 Inland Motor, Kollmorgen Corporation.
A New Design for High Speed Computerized Tomography, Maydan, et al. IEEE Transactions on Nuclear Science, vol. NS-26, No. 2, Apr. 1979.

*Primary Examiner*—David P. Porta
*Assistant Examiner*—Kim-Kwok Chu
*Attorney, Agent, or Firm*—Fay, Sharpe, Beall, Fagan, Minnich & McKee

[57] ABSTRACT

A toroidal x-ray tube (I) is supported (II) for rotation about a horizontal axis (170), translation along a vertical axis (172), and translation along a horizontal axis (174). The x-ray tube includes a toroidal housing (A), an annular anode (B), and a cathode (0) which rotates a beam of electrons around the annular anode. A plurality of parallel connected voltage sources ($90_1$, $90_2$, ..., $90_n$) provide a sufficiently high bias voltage between the electron source and the anode that x-rays are generated. The x-ray beam passes through a compensator crystal (62), an annular window (20), a collimator (132), through a subject received in a central bore (26) of the x-ray tube, and impacts an arc segment of radiation detectors (130). The x-ray detectors are stationarily mounted outside of the plane of the annular window (FIGS. 2 and 7), nutate into the plane of the windows opposite of the origin of the x-ray beam (FIG. 6), rotate in part (FIG. 9) or rotate in full (FIG. 8) Angular position monitors (58, 154) determine the angular position of the cathode assembly, hence the x-ray beam, and the angular position of the detectors in the rotating detector embodiment.

23 Claims, 9 Drawing Sheets

COMPUTERIZED TOMOGRAPHIC SCANNER HAVING A TOROIDAL X-RAY TUBE WITH A STATIONARY ANNULAR ANODE AND A ROTATING CATHODE ASSEMBLY

This application is a continuation-in-part of application Ser. Nos. 07/817,294, now U.S. Pat. No. 5,241,577; 07/817,295, now U.S. Pat. No. 5,200,985; and 07/817,296, abandoned on Aug. 20, 1993; all filed Jan. 6, 1992.

BACKGROUND OF THE INVENTION

The present invention pertains to the art of diagnostic imaging. It finds particular application in conjunction with CT scanners for generating images of interior regions of human patients and will be described with particular reference thereto. However, it is to be appreciated, that the present invention will also find application in conjunction with industrial CT, quality assurance, and other types of x-ray diagnostic imaging, x-ray generation applications, and the like.

Typically, a patient is positioned in a prone position on a horizontal couch through a central bore of a CT scanner. An x-ray tube mounted on a rotatable gantry portion is rotated around the patient at a high rate of speed. For faster scans, the x-ray tube is rotated more quickly. However, rotating the x-ray tube more quickly decreases the net radiation per image unless the x-ray output of the x-ray tube is increased. As CT scanners have become faster, larger x-ray tubes which generate more radiation per unit time have been required. The high gantry rotational speeds, of course, cause high inertial forces during rotation.

High performance x-ray tubes for CT scanners and the like commonly include a stationary cathode and a rotating anode disk, both enclosed within an evacuated housing. When higher intensity x-ray beams are generated, there is more heating of the anode disk. In order to provide sufficient time for the anode disk to cool by radiating heat through the vacuum to surrounding fluids, x-ray tubes with progressively larger anode disks have been built.

The larger anode disks require larger x-ray tubes which do not readily fit in the small confined spaces of existing CT scanner gantries In a fourth generation scanner, the incorporation of a larger x-ray tube and heavier duty support structure requires moving the radiation detectors to a larger diameter. If the distance from the x-ray focal spot to the collimator is too short, the x-ray penumbra and beam divergence cause a degradation in image quality. Not only is a larger x-ray tube required, larger heat exchange structures are required to remove the larger amount of heat which is generated. Thus, as the CT scanners have become faster, they have become more massive, hence more difficult to move and install.

Rather than rotating a single x-ray tube around the subject, others have proposed using a switchable array of x-ray tubes, e.g. five or six x-ray tubes in a ring around the subject. However, unless the tubes rotate only limited data is generated and only limited image resolution is achieved. If the x-ray tubes rotate, similar mechanical problems are encountered trying to move all the tubes quickly.

Still others have proposed constructing an essentially bell-shaped, evacuated x-ray tube envelope with a mouth that is sufficiently large that the patient can be received in the well of the tube. An x-ray beam source is disposed at the apex of the bell to generate an electron beam which impinges on an anode ring at the mouth to the bell. Electronics are provided for scanning the x-ray beam around the evacuated bell-shaped envelope. One problem with this design is that it is only capable of scanning about 210°. Another problem is that the very large evacuated space required for containing the scanning electron beam is difficult to maintain in an evacuated state. Troublesome and complex vacuum pumping systems are required. Another problem is that no provision can be made for off-focus radiation. Another problem resides in its large physical size.

Messrs. Mayden, Shepp, and Cho in "A New Design For High-Speed Computerized Tomography", IEEE Transactions on Nuclear Science, Vol. NS-26, No. 2, April 1979, proposed reducing the size of the conical or bell-shaped tube discussed above by rotating the cathode around the large diameter anode ring. However, their design had several engineering deficiencies and was not commercially produced.

The present invention contemplates a new and improved CT scanner which overcomes the above-referenced problems and others.

SUMMARY OF THE INVENTION

In accordance with the present invention, a CT scanner is provided. A generally toroidal x-ray tube defines an internal bore of sufficient diameter for passing an imaged region of a subject therethrough. The toroidal x-ray tube generates a generally fan shaped x-ray beam from at least a multiplicity of locations therearound. The beam is directed across the central bore from an apex location in the x-ray tube. A mounting means mounts the toroidal x-ray tube. The radiation detection means spans at least an arc for detecting the x-ray beam after it has passed through the imaged subject region in the bore. An x-ray beam apex location determining means determines an angular position of the x-ray beam apex location. An image reconstruction means which is connected with the radiation detection means of the x-ray beam apex location determining means reconstructs an image representation of the imaged region of the subject.

In accordance with a more limited aspect of the present invention, the toroidal x-ray tube includes a generally toroidal housing having an evacuated interior. An annular anode surface is mounted within the toroidal housing interior in thermal communication with a cooling fluid passage through which cooling fluid is circulated to remove excess heat from the anode surface. The anode surface may be a single, continuous annulus or can be assembled from a plurality of segments A cathode assembly which is disposed within the toroidal housing includes a means for emitting electrons to form an electron beam that strikes the anode surface A means is provided for moving the electron beam to at least a multiplicity of points around the anode.

In accordance with a more limited aspect of the present invention, the cathode assembly of the x-ray tube is rotatably mounted within the toroidal housing. The means for moving the electron beam includes a means for rotating the cathode assembly.

In accordance with a more limited aspect of the present invention, a compensator and a collimator are mounted for rotation with the cathode assembly and the x-ray source.

In accordance with another more limited aspect of the present invention, the cathode assembly includes a multiplicity of electron emitting means arranged in an angular ring within the housing. The electron beam moving means includes means for selectively causing each of the electron emitting means to emit a beam of electrons which impact the anode surface to generate the x-ray beam.

In accordance with another aspect of the present invention, the housing defines an annular window facing toward a central axis of the bore. An annular shutter member is disposable across the window for blocking the emission of x-rays therefrom. A shutter moving means selectively moves the shutter member into and out of the x-ray blocking relationship with the window.

In accordance with another more limited aspect of the present invention, the radiation detection means includes a ring of x-ray detectors disposed adjacent but offset from a plane defined by the annular window In accordance with a yet more limited aspect of the present invention, the radiation detecting means includes a ring of radiation detectors and a nutating means for selectively nutating a portion of the detector ring opposite the detected x-ray beam apex location into a plane defined by the window.

In accordance with another more limited aspect of the present invention, the radiation detection means includes an arc of radiation detectors that are mounted for rotation around the bore of the x-ray tube. The detector rotation control means controls rotation of the detector arc such that the detector arc is maintained opposite to the determined radiation beam apex location.

In accordance with another more limited aspect of the present invention, the x-ray beam apex location determining means includes a laser gyro for monitoring an angular position of the rotatable cathode assembly.

In accordance with another more limited aspect of the present invention, the radiation detection means includes a plurality of scintillation crystals which are rotatably mounted to the toroidal x-ray tube for rotation around the central bore. A ring of opto-electrical transducers are stationarily mounted adjacent the toroidal housing in optical communication with the scintillation crystals. In this manner, a corresponding fraction of the opto-electrical transducers are coupled in an optical communication with the scintillation crystal arc.

In accordance with another more limited aspect of the present invention, a means is provided for controlling the electron emitting means such that the generated beam of x-rays has one of at least two selectable different energies.

In accordance with another more limited aspect of the present invention, a plurality of voltage sources are connected in parallel with relatively high potential between the electron emitting means and the anode surface. There is a sufficiently low plurality of voltage sources that even if one voltage source should fail, the remaining voltage sources provide the high potential between the electron emitting means and the anode surface such that a useful x-ray beam current continues to be generated.

In accordance with another more limited aspect of the present invention, the x-ray tube mounting means includes a means selectively rotating the toroidal x-ray tube relative to a horizontal axis and a means for selectively translating the toroidal x-ray tube vertically. In this manner, the CT scanner is adapted to reconstructing an image representation of an imaged region of a standing subject.

One advantage of the present invention resides in its high x-ray power density.

Another advantage of the present invention resides in its lighter weight and manufacturing simplicity.

Another advantage of the present invention resides in its high scanning speeds.

Another advantage of the present invention resides in long tube life, augmented by ready field repairability.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
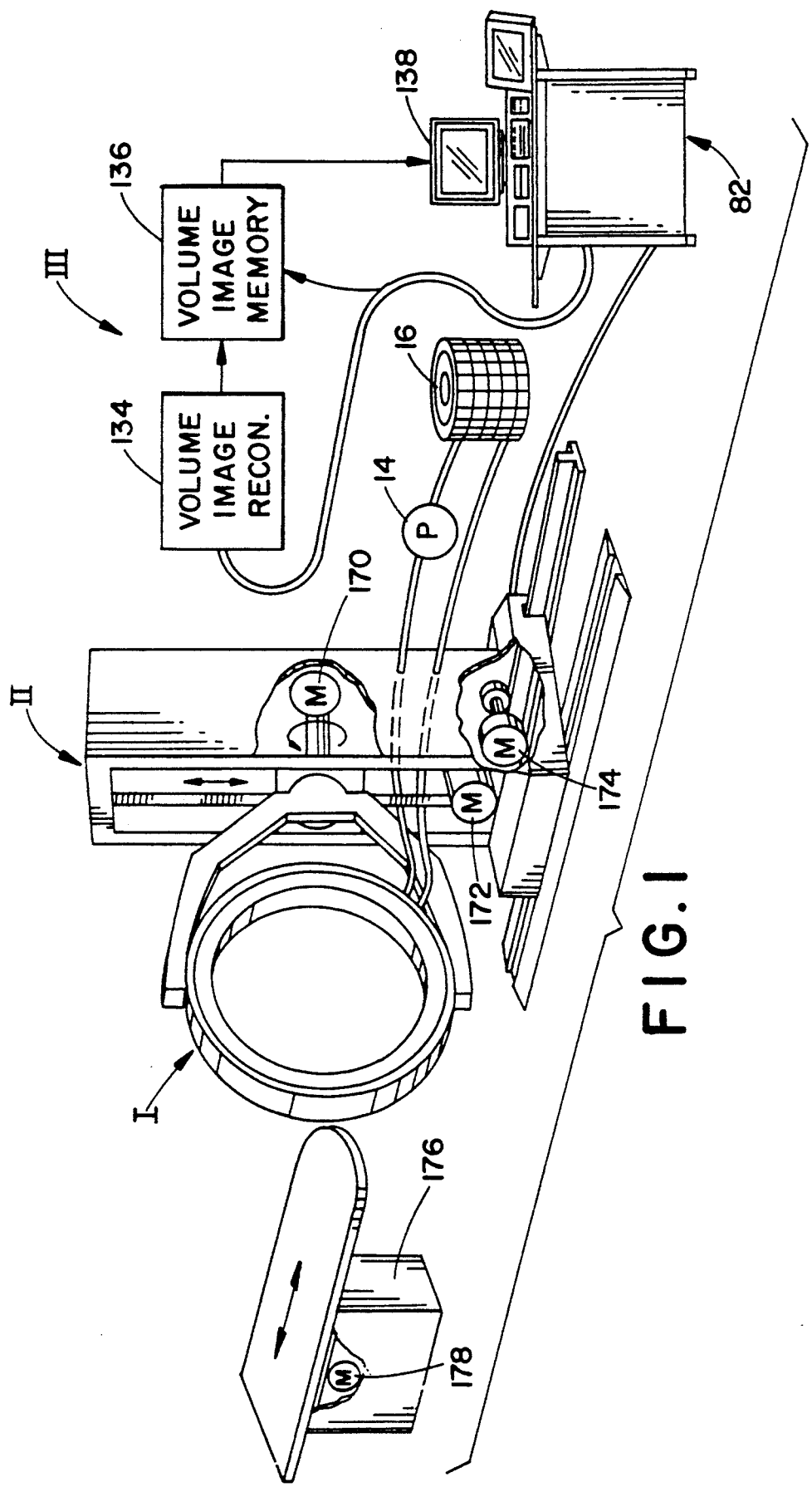
FIG. 1 is a perspective view of a CT scanner system in accordance with the present invention.

With reference to FIG. 1, a CT scanner includes a toroidal ring x-ray tube I which is mounted on a mounting means or assembly II. An electronic section III provides operating power and control signals to the ring tube and the mounting assembly II and receives data therefrom to reconstruct into an electronic image representation.

Figure 2:
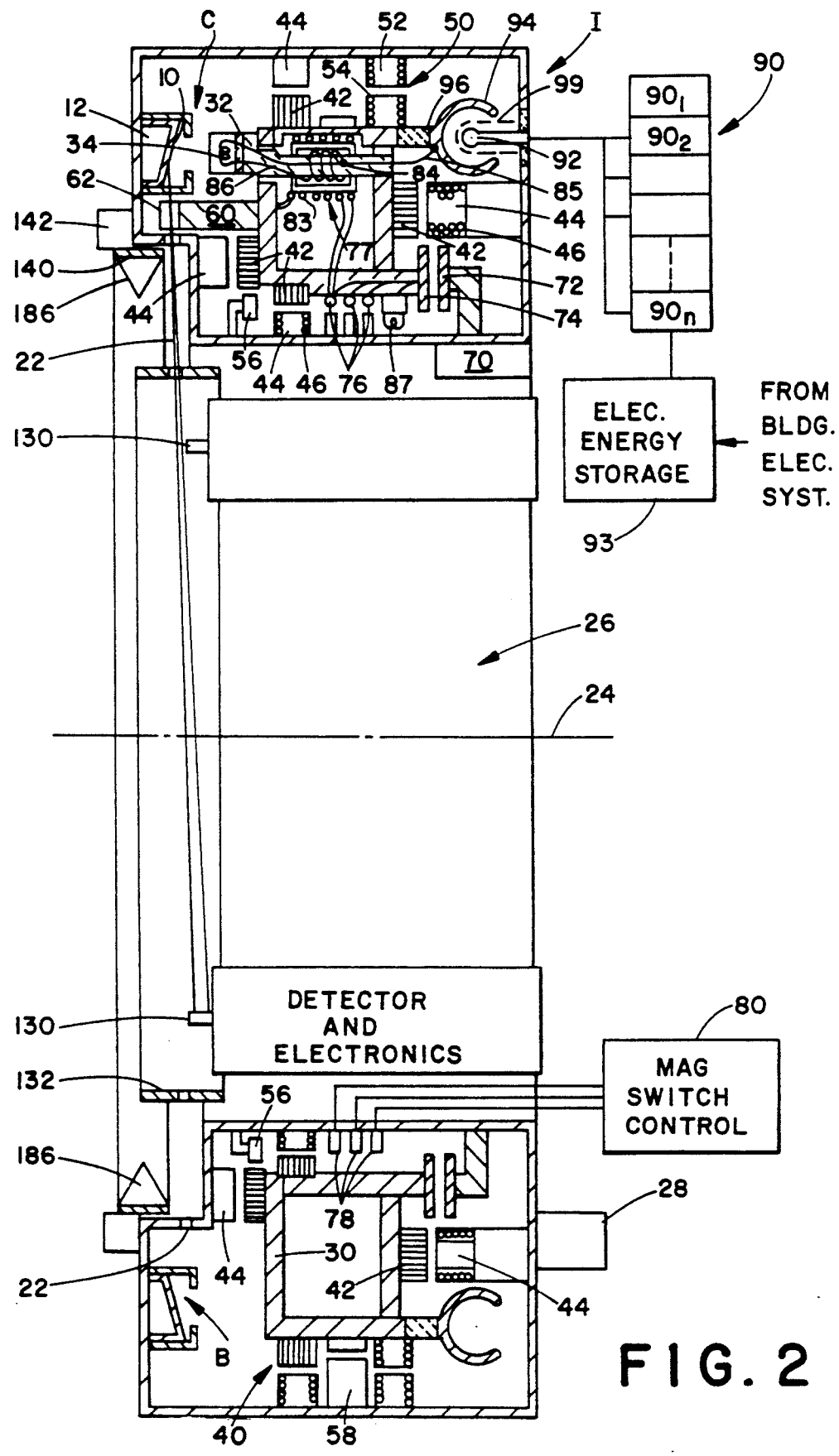
FIG. 2 is a transverse, cross-sectional view of the x-ray source and radiation detector portion of the CT scanner of FIG. 1.

With continuing reference to FIG. 1 and further reference to FIG. 2, the ring tube I includes a toroidal housing A which defines a large, generally donut-shaped interior volume. An anode B is mounted within the toroidal housing interior volume and extends circumferentially therearound. A cathode means C is disposed within the toroidal housing interior space for generating at least one beam of electrons. A means D selectively rotates the electron beam around the anode B.

More specifically, the anode B is a tungsten toroid having a tungsten face 10 upon which the electron beam impinges. The housing and the anode define an annular cooling fluid path or channel 12 in intimate thermal Communication with the anode face, specifically along an opposite surface of the anode. The anode can be a large continuous member or assembled form multiple sections. Optionally, the anode can have internal passages, fins, and the like to promote thermal communication with the cooling fluid. A fluid circulating means 14 circulates the fluid through the stationary anode and housing to a heat exchanger 16 to keep the target anode cool.

A window 20 is defined in the housing closely adjacent to the target anode B. The window is positioned such that an x-ray beam 22 generated by interaction of the electron beam and the tungsten target anode is directed transverse to a central axis 24 of the toroidal tube through a central bore 26. Preferably, the window is constructed of a sheet of stainless steel which is TIG welded in a vacuum sealed relationship to preferably steel surrounding portions of the toroidal housing A. Preferably, the housing at least adjacent to the anode is constructed of beryllium to reduce the intensity of off-focal radiation. A vacuum means, preferably one or more ion pumps 28, is interconnected with the housing to maintain the vacuum within the housing.

In the embodiment of FIGS. 1 and 2, the cathode assembly includes an annular ring 30 which extends around the interior of the toroidal housing. One or more cathode cups 32 are mounted on the cathode ring. The cathode cups 32 each includes a cathode filament 34.

In the preferred embodiment, each of the cathode cups 32 has a preselected focus characteristic. In this manner, different dimensions of the x-ray beam focal spot are chosen by selecting among the cathode cups. Optionally, there are multiple cathode cups focused with the most commonly used dimensions to provide a back-up cathode cup in the event the first cathode cup should burn out.

The cathode ring 30 is rotatably supported within the housing by a bearing means 40. In the preferred embodiment, the bearing means is a magnetic levitation bearing. Thin rings 42 of silicon iron or other material, suitably prepared to be insulating in vacuum, are longitudinally stacked to form cylinders for the radial portion of the bearing. Thin hoops of silicon iron or other material, also suitably prepared for use in vacuum, are assembled to form tightly nested cylinders for the axial portion of the bearing. Passive and active elements, i.e. permanent magnets 44 and electromagnets 46, are controlled by proximity sensors and suitable feedback circuits to balance attractive forces and suspend the cathode ring accurately in the center of the toroidal vacuum space and to center the cathode ring axially. A brushless, large diameter induction motor 50 includes a stator 52 stationarily mounted to the housing and a rotor 54 connected with the cathode ring. The motor causes the cathode assembly C to rotate at a selected speed through the toroidal vacuum of the housing. Mechanical roller bearings 56 are provided for supporting the cathode ring in the event the magnetic levitation system should fail. The mechanical roller bearings prevent the cathode ring from interacting with stationary housing and other structures. A laser gyro or other angular position monitoring means 58 monitors the angular position of the cathode assembly, hence the location of the apex of the x-ray beam on the anode surface.

Adjacent each cathode cup assembly 32, there is a support 60 which rotates with the cathode cup. The support 60 carries a filter or compensator 62 which is mounted to the support adjacent to the window for filtering the generated x-ray beams to provide beam hardness correction or the like. Preferably, the filter is a shaped block of beryllium oxide (BeO). Optionally, structures for defining fan beam angle or width may also be mounted for rotation with the cathode cup.

A current source 70 provides an AC current for actuating the selected cathode cup. The AC current is passed to a stationary, annular capacitor plate 72 mounted inside the housing. A matching, rotating capacitor plate 74 supported by the cathode ring is mounted closely adjacent to the stationary cathode plate. The rotating cathode plate is electrically connected with a series of magnetically controlled switches 76. Each of the switches 76 is connected by an isolation transformer 77 with one of the cathode cups or circuitry for controlling a bias to any grids on the cathode cups. A plurality of annular electromagnets 78 are stationarily mounted along the housing. An electrical control means so on an operator control 82 permits actuation of one or more of the electromagnets for opening and closing the magnetically controlled switches to select among the cathode cups and any biasing potentials.

The isolation transformer 77 includes a primary winding 83 connected with the switch 76 and the annular ring 30. A secondary 84 is connected with one end of the cathode filament 34 and a high voltage supply line 85 which biases the cathode cup to $-100$ to $-200$ kV. A ceramic insulator 86 insulates the annular ring 30 from the cathode cup and the high voltage supply line 85. A filament 87 that is connected between the annular ring 30 and the current source 70 boils off electrons that are transferred to the housing. This transfers any charge accumulated on the annular ring and holds the housing and annular ring at the same potential.

Alternately, external switches provide power to one of a plurality of stationary capacitor rings. Each of a matching plurality of rotating rings is connected with a different cathode cup. As yet another alternative, the capacitive coupling may be replaced by an inductive coupling, such as a stationary annular primary winding which is mounted closely and adjacent and across an air gap from the rotating annular secondary winding.

The anode and the cathode are maintained at a high relative voltage differential, typically on the order of 130 kV. In the preferred embodiment, the stationary housing and the anode are held at ground, for user safety. The rotating cathode assembly is biased on the order of $-130$ kV relative to the housing. To this end, a high voltage section 90 generates a high voltage which is applied to a hot cathode 92 of a vacuum diode assembly. The hot cathode filament 92 is preferably of a low work function type.

Preferably, the high voltage section 90 is a multiplicity of compact, three phase, high-frequency voltage generators $90_1$, $90_2$, ... $90_n$ connected with parallel current sharing outputs. In this manner, should one of the power supplies fail, the remaining power supplies operated in parallel maintain an adequate x-ray current albeit at a reduced mA such that the CT scanner is still operable at a lower energy level. Each generator has a minimal output capacitance to minimize energy storage and reduce damage if arcing should occur. The low capacitance also enables higher speed kV switching for dual energy applications. To reduce peak power demands from the electrical system of the medical facility, the voltage generators 90 are connected with an energy storage device 93, such as storage batteries or capacitors. The energy storage device draws current to recharge at a relatively low rate and supplies current at a relatively high rate during an exposure.

A circular channel of a toroidal or donut-shaped plate 94 partially surrounds the hot cathode filament. The toroidal plate is mounted to the cathode assembly for rotation therewith. Preferably, a ceramic or other thermally isolating plate or means 96 isolates the toroidal plate from the rotating annular ring 30. The current is conducted by the high voltage supply line 85 from the toroidal plate to the cathode cup. The supply line 85 is preferably a thin wire or film to limit heat transfer. A grid 99 is mounted around the hot cathode for filtering and tube current control.

Figure 3:
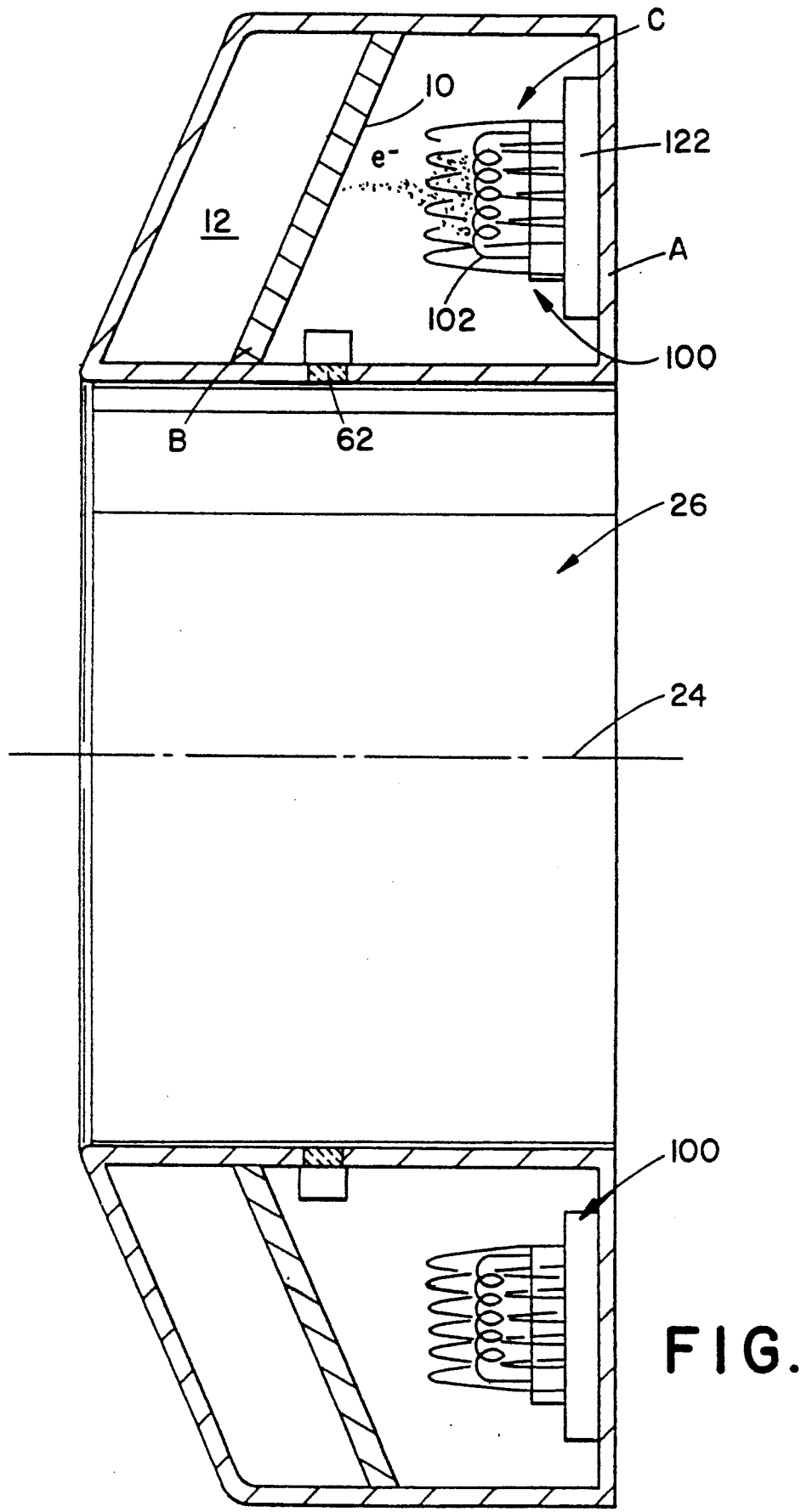
FIG. 3 is a transverse section of an alternate embodiment of the x-ray ring tube with a stationary cathode assembly.
Figure 4:
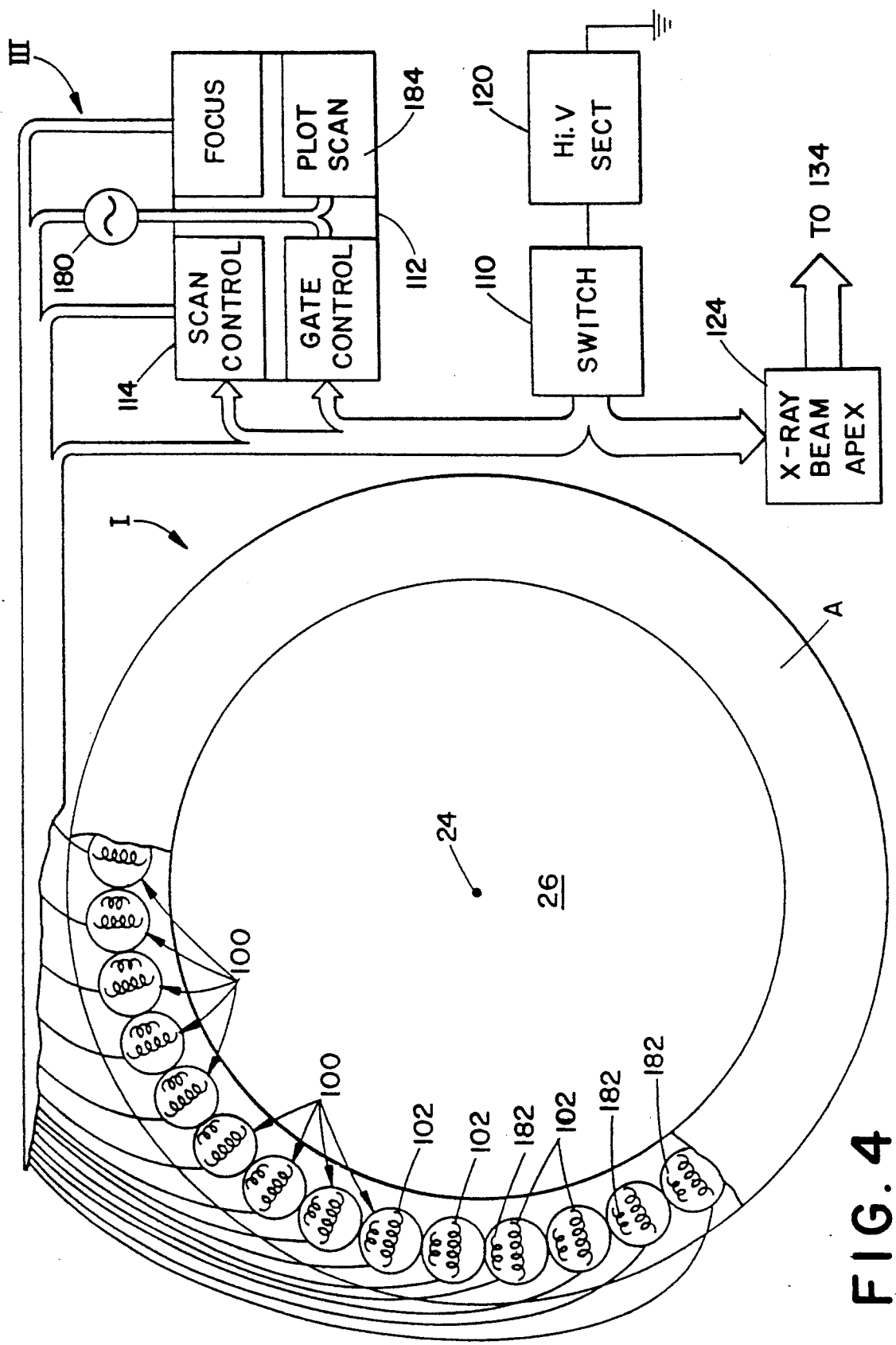
FIG. 4 is a front view in partial section with associated electronics of the ring tube of FIG. 3.
Figure 5:
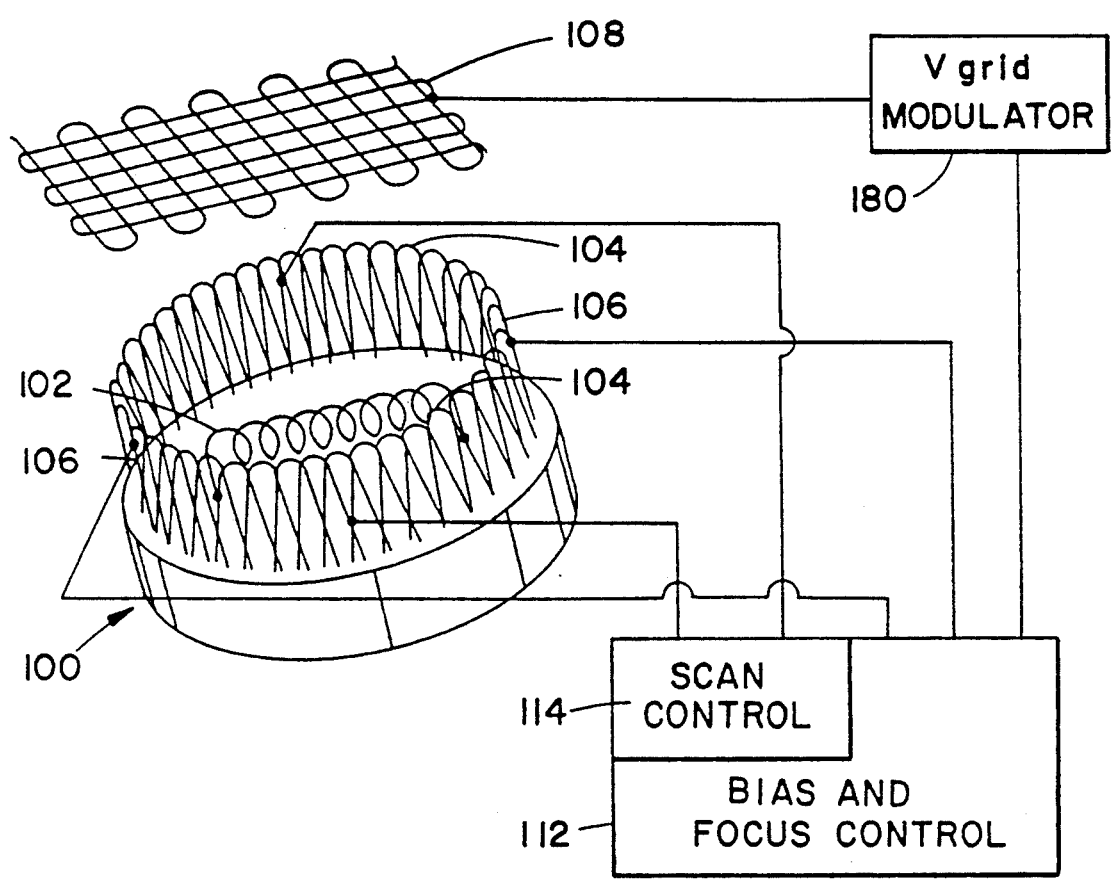
FIG. 5 is a perspective view of one of the cathode cups of FIGS. 3 and 4 with associated electronics.

In the embodiment of FIGS. 3, 4, and 5, the housing A is again toroidal. The anode B is again annular and defines a cooling path 12 with a portion of the housing. The tungsten anode face 10 is disposed toward the cathode assembly C to generate the x-ray beam when excited by an electron beam from the cathode. The cathode assembly includes a multiplicity of cathode cups 100 arranged closely adjacent to each other in a ring around the housing. Each cathode cup includes a cathode filament 102 which is heated by an excitation current to undergo thermionic emission. A grid assembly includes a pair of grids 104 for focusing the generated electron beam in a circumferential direction relative to the anode and a pair of grids 106 for focusing the electron beam in a radial direction. A gate electrode 108 selectively permits and prevents the electron beam from reaching the anode. In the preferred embodiment, a switching means 110 sequentially switches each of the gate grids 108 to permit the passage of electrons. In this manner, the electron beam is stepped, or moved in other selected patterns, around the anode.

A biasing and focusing control circuit 112 applies appropriate bias voltages to the grid pairs 104, 106 to focus the electron beam at a selected point on the anode relative to the cathode cup with a selected beam dimension. Optionally, the biasing and focusing control circuit 112 may include a scanning means 114 for gradually or incrementally shifting the bias voltage between the grids 104, 106 to sweep or scan the electron beam continuously or in a plurality of steps to a plurality of positions along an arc segment of the anode commensurate with a circumferential length of the cathode cup. Each time the switching means 110 switches to the next cathode cup, it causes the beam scanning means 114 to sweep the electron beam along each of its preselected circumferential beam positions.

A high voltage means 120 biases the cathode assembly C to a high voltage relative to the housing. A ceramic insulation layer 122 insulates the cathode cups from the housing such that the cathode cups can be maintained at a potential, on the order of $-130$ kV, is preferably held to ground and the cathode cups are biased on the order of $-130$ kV relative to the housing and the anode. Alternately, the anode may be electrically insulated from the housing and biased to a positive voltage relative to the housing. In such an embodiment, care must be taken that the cooling fluid is dielectric such that the cooling fluid does not short the anode to the housing.

The filaments of all the cathode cups are preferably driven concurrently. The switching means 110 further switches the high voltage supply 120 sequentially to each of the cathode cups 100. In this manner, only one or a small group of cathode cups at time is maintained at a sufficiently high voltage relative to the anode to cause an x-ray beam and the generation of x-rays. Of course, either the grid 108 or the individual cathode cup biasing may be used individually to control the electron and x-ray beams. An x-ray beam apex location means 124 determines the location of the electron beam on the anode, hence the origin of the x-ray beam, from the output of switching means 110.

Each individual cathode segment or cup preferably is constructed with radial slots with series or parallel connected filaments in each slot. Such slot and filament portions naturally provide line focus electron beams desirable for target loading when the grid voltage is removed from the desired segment. This radially slotted section may be divided in half and appropriately insulated to facilitate sweeping the focal spot across the anode track. These halves can also be used to alter the size of the focal spot.

An additional refinement may be obtained by heating the filament or, more generally, the electron emitter by a second cathode structure behind the emitter and accelerated by a more modest potential and a locally controlled grid in a similar manner to the main cathode structure. One of the benefits achieved by this construction is that low temperature, low work function filaments may be employed. This lowers the heating current requirement substantially. The electron emitters can be heated very uniformly to achieve a very uniform focal spot. These emitters furthermore may be constructed of tungsten ribbon or other suitable shaped material of low effective thermal mass so that an emitter may be boosted to operating temperature very quickly, requiring only grid control of the second filament to achieve markedly lower heating energy to the electron emitter and a large increase in reliability.

With reference again to FIGS. 1 and 2, a ring of detectors 130 are supported with a housing such that they remain stationary as the cathode assembly C rotates. A collimator or other off-focal radiation limiting means 132 is positioned relative to the point at which the electron beam impacts the anode such that the resultant collimated radiation beam 22 is incident on the detectors. The detectors are positioned as close as possible to the collimator such that the fan beam of radiation is, as close as possible, orthogonal to the central axis 24 of the ring tube. For ring tubes with an internal bore large enough to receive the human torso and an x-ray beam on the order of a millimeter thick, the x-ray beam can be defined by collimation to within a half a degree or less of orthogonal to the central axis. Preferably, the patient and the x-ray source move relative to each other along the central axis 24 such that the detected radiation data represents generally a spiral pattern through the patient. A conventional volume imaging means 134 reconstructs the spiral data from the detectors using the beam apex location information into a three-dimensional image representation which is stored in a volume image memory 136. In spiral imaging, it will be appreciated that the continuous axial movement causes each sampling of the detectors to be in a different axial position, i.e. in a different plane. The adjustments made by the conventional volume imaging means 134 to interpolate the spiral data into parallel plane data for reconstruction can also make an appropriate adjustment for the angular offset between the axis and the x-ray beam. Optionally, a cone beam algorithm is used along with the interpolation of data. In single slice imaging, an analogous correction can be made. Alternately, because the angle is so small, the image can be reconstructed using conventional planar image reconstruction algorithms without compensating for the effective increase in the width of the slice.

The operator console 82 contains appropriate controls for withdrawing selected portions of the volume image representation from the volume image memory 136 for display on a video monitor 138 or other appropriate displays. As is conventional in the art, the operator control means 84 may select planes along orthogonal axes through the volume image data, planes skewed to the orthogonal axes, 3D type images with appropriate surface shading to provide the two-dimensional display with the appearance of three dimensions, and the like.

A shutter 140 is mounted for selective movement between a closed position covering the window and an open position which permits the transmission of x-rays through the window to the detector ring. The shutter ring is constructed of a radiation blocking material such that no radiation is permitted to pass therethrough when the shutter is closed. A shutter control means 142 such as a plurality of linear motors selectively slides the shutter ring between open and closed positions.

Figure 6:
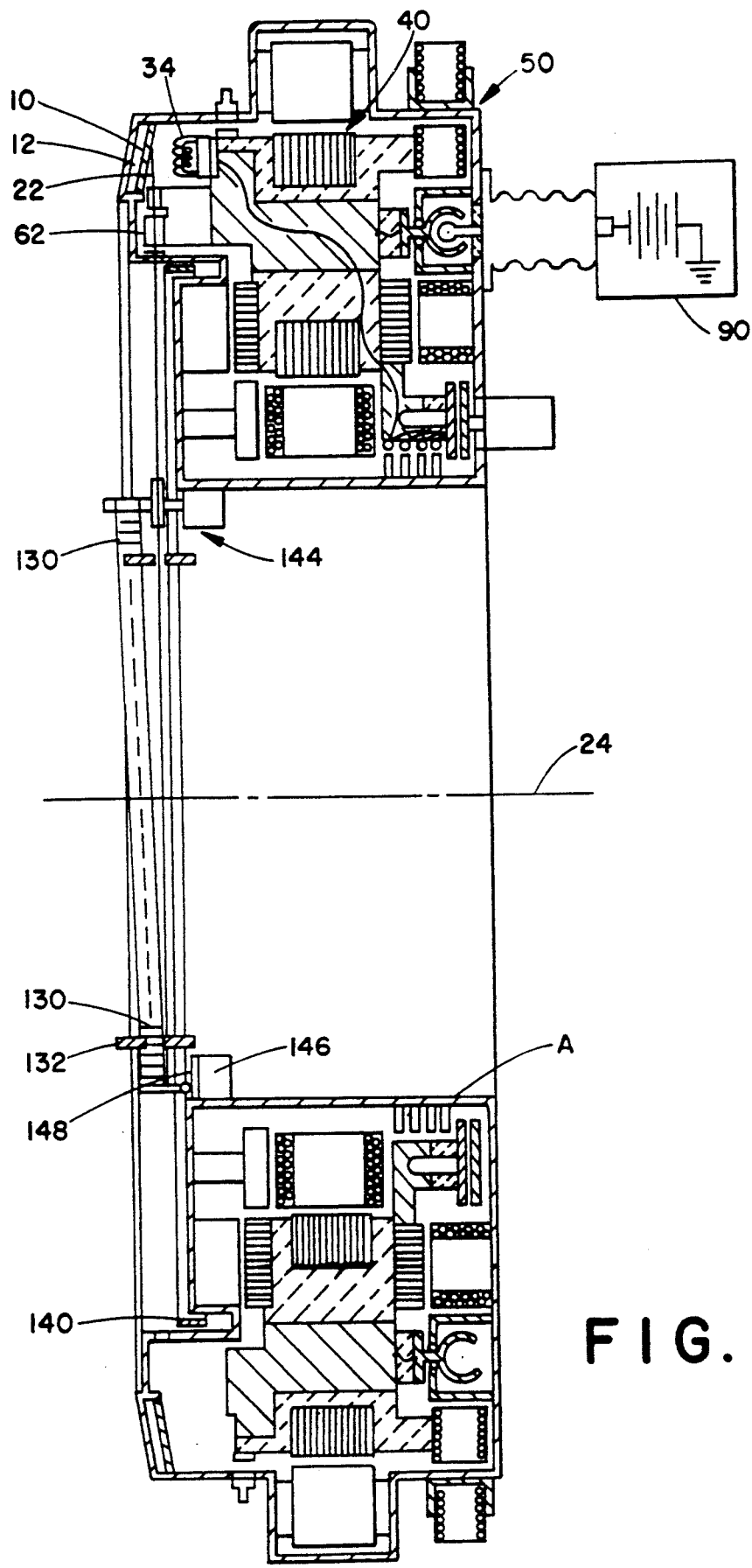
FIG. 6 is a transverse cross-sectional view of a CT scanner tube in accordance with the present invention in which a ring of non-rotating x-ray detectors nutates into a plane of the x-ray beam.

In the embodiment of FIG. 6, the collimator or off-focal radiation limiting means 132 defines the x-ray beam 22 perpendicular to the central axis 24. The ring of radiation detectors 130 is fixed against rotation. A nutating means 144 moves the portion of the radiation detectors generally parallel to the central axis 24 such that the detectors are positioned in front of the window 20 opposite the apex location of the radiation beam. That portion of the detector ring which is positioned adjacent the point at which x-rays are being generated is offset from the plane of the x-ray beam such that the x-ray beam does not pass through those detectors.

In the illustrated embodiment, the nutating means 144 includes a wobble-plate type construction. More specifically, an annular motor 146 rotates an annular Cam surface 148 Which is mounted at an angle to the central axis 24. As the angled plate or cam surface rotates, it rotates the portion of the detector ring which is cammed into alignment with the x-ray beam. Optionally, other devices can be provided for nutating the detector ring. For example, the detector ring can be made in segments which are moved parallel to the central axis 24 into and out of the plane of the x-ray beam. As another example, magnetic cams are used to produce the nutating movement.

Figure 7:
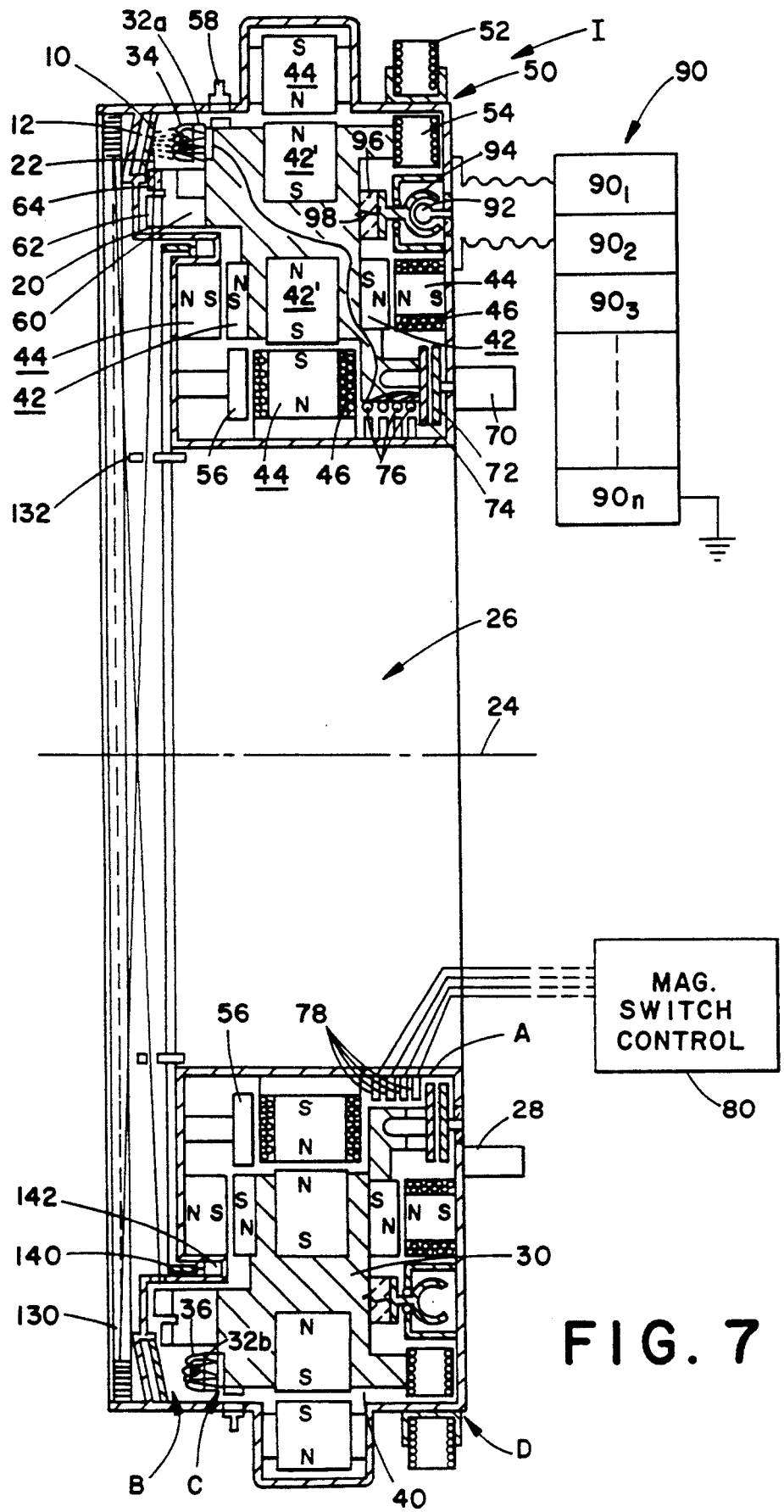
FIG. 7 is an alternate embodiment of a CT scanner in accordance with the present invention.

In the alternate embodiment of FIG. 7, the x-ray beam is directed and collimated at a slight angle to the central axis 24 to impact a detector ring located near the exterior diameter of the ring tube. A plurality of cathode cups 32a and 32b are provided. Grids 36 filter, gate, and control the emitted electron beam. The cathode assembly is illustrated as being suspended by repulsive interaction with permanent magnets 42' rather than attractive interaction with fields induced in the silicon iron hoops.

Figure 8:
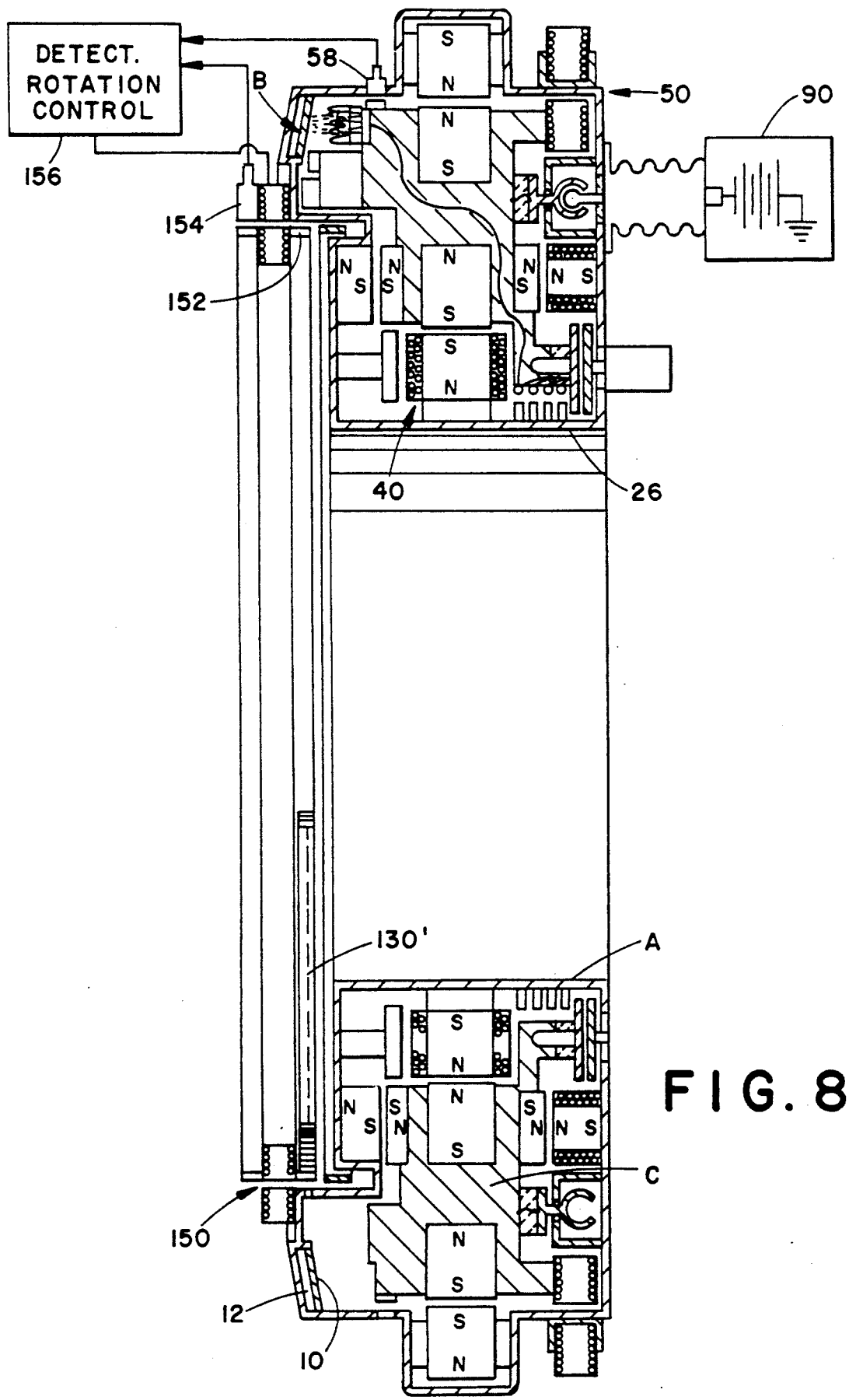
FIG. 8 is a transverse sectional view of an alternate embodiment of the x-ray generating and detecting portion of a third generation CT scanner in accordance with the present invention.

In the embodiment of FIG. 8, a large diameter annular motor 150 rotates a partial ring of x-ray detectors 130, Optionally, a collimator, filter, or compensating means 152 may be mounted to rotate opposite the detector arc. A first angular position detecting means 58, preferably a laser gyro, detects the angular position of the cathode assembly B. A second angular position detecting means 154 detects the angular position of the detector arc. A rotation controller 156 controls the operation of the motor 150 in accordance with the input from the two position detectors such that the detector arc rotates at precisely the same speed as the x-ray beam.

Figure 9:
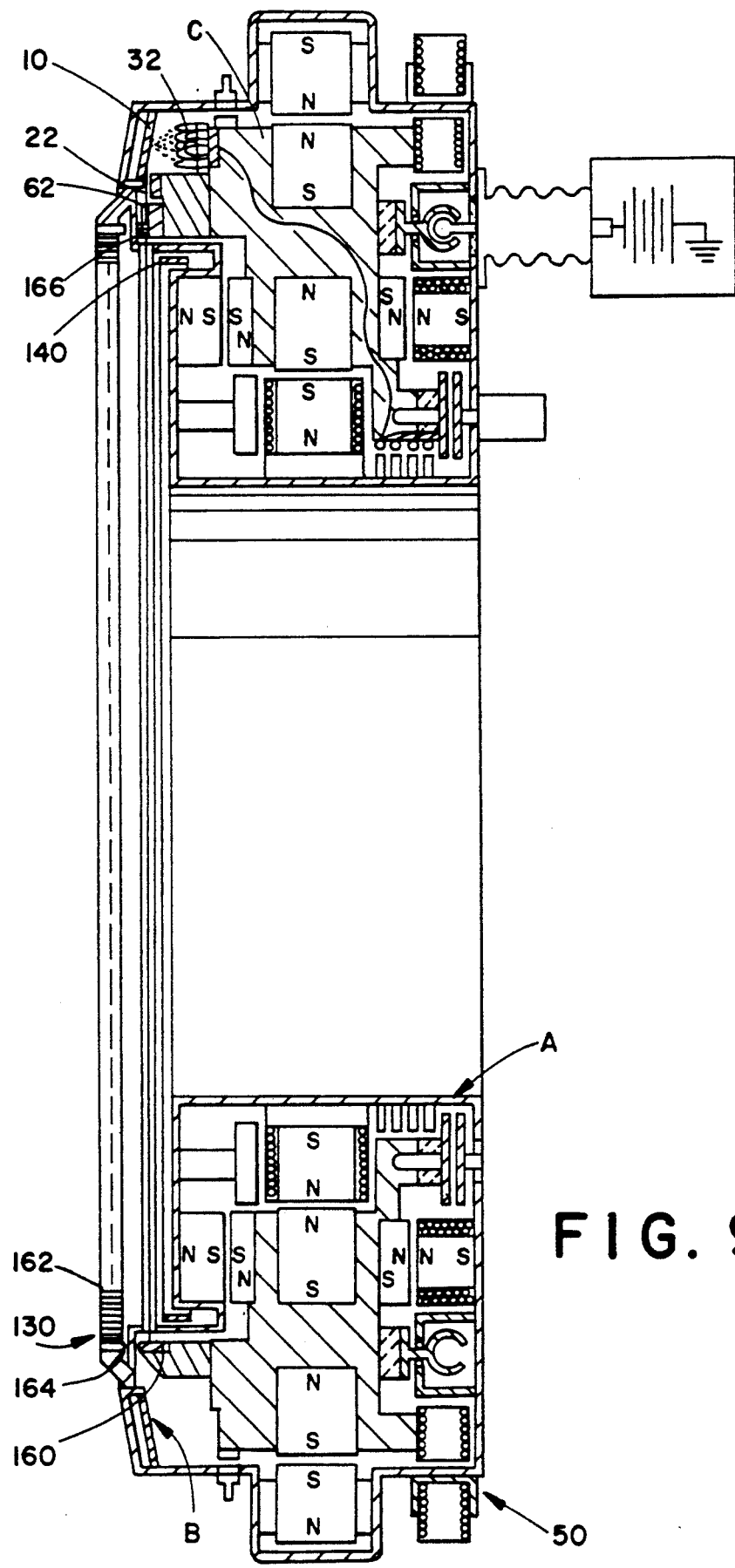
FIG. 9 is a transverse sectional view of another alternate embodiment of a third generation type CT scanner in accordance with the present invention.

In the embodiment of FIG. 9, the x-ray detector means 130 includes an arc of scintillation crystals 160 and a ring of opto-electrical transducers, such as photodiodes 162. At least the scintillation crystal or other x-ray to light transducer means is mounted along an arc segment to the cathode assembly C opposite one or more cathode filaments. As the cathode assembly rotates, the arc of scintillation crystals rotates therewith. The photodiodes are mounted stationarily on the exterior of the housing. An optical coupling 164 transfers light from the rotating scintillation crystals to the stationary photodiodes as the cathode assembly rotates. A light amplifier is advantageously positioned between the scintillation crystals and the photodiodes. In the preferred embodiment, the scintillation crystals extend along only an arc segment such that the radiation does need to pass through the scintillation crystals before striking the patient. In areas beyond the scintillation crystal arc, a shielding means or ring 166 is provided for shielding the optical transfer means 164 for receiving light or other incident radiation.

With reference again to FIG. 1, the mounting means II includes a rotating means 170 for selectively rotating the ring tube I about a horizontal axis. A vertical translating means 172 selectively translates the ring tube along a vertical axis. It is to be appreciated, that the rotating means can position the ring tube horizontally such that the vertical translating means 172 translates the ring tube along a standing patient. This enables patients to be imaged in a standing orientation to reflect the natural effects of gravity on the patient's body.

A horizontal translating means 174 selectively translates the ring tube along a horizontal direction. When the rotating means 170 positions the ring tube in a vertical position, the horizontal translating means can translate the ring tube along a stationary patient in a prone position, e.g. supported on a patient couch 176 Optionally, the couch 176 includes a horizontal translating means 178 for moving a top surface of the couch, hence the patient, along a horizontal axis.

The electronic section III further includes means for causing the ring tube to generate a dual or multiple energy x-ray beam. In the embodiment of FIG. 5, the dual or multiple energy means includes a grid potential modulating means 180, such as an oscillating voltage source, for oscillating the potential applied to the gating grid of the active electron source. By modulating the gate potential voltage, the flow of electrons, hence the energy of the electron beam is selectively modulated.

In the embodiment of FIG. 2, the dual energy means can include high and low energy electron sources disposed alternately around the cathode ring. As yet another alternative, each cathode cup 100 can include a second, lower energy filament. As yet another alternative, a grid is disposed around the hot cathode 92 to control the flow of energy to the cathode.

A pilot scan means 184 selectively gates each of the electron sources to emit an electron beam as it passes a preselected point on the anode, typically top dead center. This causes a fixed orientation x-ray beam to be generated for use in pilot scans. Preferably, the patient couch translating means 178 has a variable horizontal translation speed such that each gating of an electrode beam from the preselected point on the anode occurs in preselected steps along the patient.

With reference again to FIG. 2, a plurality of lasers 186 are mounted on the shutter. The lasers emit beams of optically visible light in the plane of the window 20 for providing a visual indication of where the slice will be taken to the operator.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A CT scanner comprising:
   a toroidal x-ray tube defining a central bore of sufficient diameter for passing an imaged region of a subject therethrough, the toroidal x-ray tube generating a fan-shaped x-ray beam from a multiplicity of apex locations therearound, which x-ray beam is directed across the central bore;
   an x-ray tube mounting means for mounting the toroidal x-ray tube;
   a plurality of scintillation crystal means spanning at least an arc for converting a received portion of the x-ray beam after it is passed through the imaged subject region in the central bore into light, the scintillation crystal means being rotatably mounted to the toroidal x-ray tube for rotation around the central bore thereof;
   a ring of opto-electrical transducers for converting received light into corresponding electrical signals, the opto-electrical transducers being stationarily mounted with the toroidal housing in optical communication with the scintillation crystal means such that a corresponding fraction of the opto-electrical transducers are in optical communication with the arc of scintillation crystal means;
   an x-ray beam apex location determining means for determining an angular position of the x-ray beam apex location;
   an image reconstruction means operatively connected with the opto-electric transducers and the x-ray beam apex location determining means for reconstructing an image representation of the image region of the subject.

2. The CT scanner as set forth in claim 1 wherein the x-ray tube includes:
   a generally toroidal housing having an evacuated interior;
   an annular anode surface mounted within the toroidal housing interior, the anode surface being in thermal communication with a cooling fluid passage for circulating cooling fluid contiguous to the anode surface for removing heat;
   a cathode assembly disposed within the toroidal housing including a means for emitting electrons to form an electron beam that strikes the anode surface;
   a means for moving the electron beam to at least a multiplicity of points around the anode surface.

3. The CT scanner as set forth in claim 2 wherein the x-ray tube further includes:
   a rotatable mounting means for rotatably mounting the cathode assembly within the toroidal housing; and,
   wherein the electron beam moving means includes a means for rotating the cathode assembly.

4. The CT scanner as set forth in claim 2 wherein the cathode assembly includes a multiplicity of electron emitting means arranged in an annular ring within the housing opposite the anode surface and wherein the electron beam moving means includes a means for selectively causing each of the electron emitting means to emit a beam of electrons which impact the anode surface to generate the x-ray beam.

5. The CT scanner as set forth in claim 2 further including a means for controlling the electron emitting means such that the x-ray beam generated by the electron beam striking the anode surface has at least two different energies.

6. The CT scanner as set forth in claim 1 wherein the image reconstruction means includes:
   a volume imager for reconstructing a three-dimensional image representation of an examined region of the subject;
   an operator control panel for selectively controlling the retrieval and display of two-dimensional representations of portions of the three-dimensional image representation.

7. The CT scanner as set forth in claim 1 wherein the toroidal x-ray tube mounting means includes:
   a means for selectively rotating the toroidal x-ray tube about a horizontal axis;
   a means for selectively translating the toroidal x-ray tube vertically, whereby the CT scanner is adapted to reconstructing an image representation of a standing subject.

8. The CT scanner as set forth in claim 7 wherein the x-ray tube mounting means further includes a means for translating the toroidal x-ray tube horizontally.

9. A CT scanner comprising:
   a toroidal x-ray tube defining a central bore of sufficient diameter for passing an imaged region of a subject therethrough, the x-ray tube including:
   a toroidal housing having an evacuated interior;
   an annular anode surface mounted within the toroidal housing interior, the anode surface being in thermal communication with a cooling fluid passage for circulating cooling fluid contiguous to the anode surface for removing heat;
   a cathode disposed within the toroidal housing for emitting electrons to form an electron beam that strikes the anode surface to generate an x-ray beam which passes across the central bore;
   a rotatable mounting means for rotatably mounting the cathode for rotation around the evacuated interior of the toroidal housing such that a location at which the electron beam strikes the anode surface is rotated through a ring of locations around the annular anode surface;
   a compensator mounted in the evacuated interior of the toroidal housing for rotation with the cathode and disposed adjacent the location at which the electron beam strikes the anode such that the generated x-ray beam passes therethrough;
   an x-ray tube mounting means for mounting the toroidal x-ray tube;
   a radiation detection means spanning at least an arc for detecting the x-ray beam after it is passed through the imaged subject region in the central bore;

an x-ray beam apex location determining means for determining angular positions of the locations at which the electron beam strikes the anode surface;

an image reconstruction means operatively connected with the radiation detection means and the x-ray beam apex location determining means for reconstructing an image representation of the image region of the subject.

10. The CT scanner as set forth in claim 9 wherein the compensator includes a beryllium oxide element.

11. The CT scanner as set forth in claim 9 wherein the radiation detection means includes:

an arc or radiation detectors;

a rotatable mounting means for mounting the arc of radiation detectors for rotation around the bore of the toroidal x-ray tube;

a detector arc rotating means for rotating the detector arc around the bore;

a detector rotation control means operatively connected with at least the x-ray beam apex location determining means for controlling the detector arc rotating means such that the detector arc is maintained generally opposite to the determined apex location.

12. The CT scanner as set forth in claim 9 wherein the housing defines an annular window facing toward a central axis of the toroidal housing bore through which the x-ray beam passes and further including:

an annular shutter member which is disposable across the window for blocking the emission of radiation therefrom; and, a means for selectively moving the shutter member into and out of the radiation blocking relationship with the window.

13. The CT scanner as set forth in claim 12 wherein the window is TIG welded to the housing.

14. The CT scanner as set forth in claim 12 wherein the radiation detection means includes a ring of radiation detectors disposed adjacent and offset from a plane defined by the annular window.

15. A CT scanner comprising:

a toroidal x-ray tube defining a central bore of sufficient diameter for receiving an image region of a subject therein, the x-ray tube including:

a toroidal housing having an evacuated interior;

an annular anode surface mounted within the toroidal housing interior, the anode surface being in thermal communication with a cooling fluid passage for circulating cooling fluid contiguous to the anode surface for removing heat;

a high energy electron beam emitting means disposed within the toroidal housing for emitting a beam of electrons which strikes the anode surface and forms a higher energy x-ray beam;

a low energy electron beam emitting means disposed within the toroidal housing for emitting an electron beam which strikes the anode surface and generates a lower energy x-ray beam, the higher and lower energy x-ray beams being directed across the central bore;

a means for moving each of the electron beams to at least a multiplicity of points around the anode surface;

an x-ray tube mounting means for mounting the toroidal x-ray tube;

a radiation detection means spanning at least an arc for detecting at least one of the higher and lower energy x-ray beams after passing through the imaged subject region in the bore;

an x-ray beam apex location determining means for determining angular positions at which the beams of electrons strike the anode surface;

an image reconstruction means operatively connected with the radiation detection means and the x-ray beam apex location determining means for reconstructing at least one image representation of the image region of the subject.

16. A CT scanner comprising:

a toroidal x-ray tube defining a central bore of sufficient diameter for passing an imaged region of a subject therethrough, the x-ray tube including:

a toroidal housing having an evacuated interior;

an annular anode surface mounted within the toroidal housing interior, the anode surface being in thermal communication with a cooling fluid passage for circulating cooling fluid contiguous to the anode surface for removing heat;

a cathode disposed within the toroidal housing for emitting electrons to form an electron beam that strikes the anode surface to generate an x-ray beam which passes across the central bore;

a rotatable mounting means for rotatably mounting the cathode around the evacuated interior of the toroidal housing such that a location at which the electron beam strikes the anode surface is rotated to a ring of locations around the annular anode surface;

a plurality of voltage sources which are connected in parallel to apply a relatively high potential between the cathode and the anode surface, there being a sufficiently large plurality of voltage sources that if one of the voltage sources fails, a sum of the voltages of the remaining voltage sources provides sufficient electrical energy to continue generating the x-ray beam but at a reduced power;

an x-ray tube mounting means for mounting the toroidal x-ray tube;

a radiation detection means spanning at least an arc for detecting the x-ray beam after it is passed through the imaged subject region in the central bore;

an x-ray beam apex location determining means for determining angular positions of the locations at which the electron beam strikes the anode surface;

an image reconstruction means operatively connected with the radiation detection means and the x-ray beam apex location determining means for reconstructing an image representation of the image region of the subject.

17. The CT scanner as set forth in claim 16 wherein the voltage sources are connected with a rechargeable electric power supply which provides relatively high current during generation of the x-ray beam and draws a relatively low current to recharge.

18. A CT scanner comprising:

a generally toroidal x-ray tube defining a central bore of sufficient diameter for passing an imaged region of a subject therethrough, the x-ray tube including:

a toroidal housing having an evacuated interior, the housing defining an annular window facing toward a central axis of the central bore through which the x-ray beam passes;

an annular anode surface mounted within the toroidal housing interior, the anode surface being in thermal communication with a cooling fluid passage for circulating cooling fluid contiguous to the anode surface for removing heat;

a cathode assembly disposed within the toroidal housing including a means for emitting electrons to form an electron beam that strikes the anode surface to generate an x-ray beam that passes through the annular window and across the central bore;

a means for moving the electron beam to at least a multiplicity of points around the anode surface;

an annular shutter member which is disposable across the window for blocking the x-ray beam from passing therethrough;

a means for selectively moving the shutter member into and out of the x-ray beam blocking relationship with the window;

an x-ray tube mounting means for mounting the toroidal x-ray tube;

an x-ray beam apex location determining means for determining an angular position at which the electron beam strikes the anode surface;

a radiation detection means for detecting the x-ray beam after it is passed through the imaged subject region in the bore, the radiation detection means including:

a ring of radiation detectors;

a nutating means for selectively nutating a portion of the detector ring opposite the angular position in which the electron beam strikes the anode surface;

an image reconstruction means operatively connected with the radiation detection means and the x-ray beam apex location determining means for reconstructing an image representation of the image region of the subject.

19. A CT scanner comprising:

a toroidal x-ray tube defining a central bore of sufficient diameter for passing an imaged region of a subject therethrough, the x-ray tube including:

a generally toroidal housing having an evacuated interior;

an annular anode surface mounted within the toroidal housing interior, the anode surface being in thermal communication with a cooling fluid passage for circulating cooling fluid contiguous to the anode surface for removing heat;

a cathode disposed within the toroidal housing for emitting electrons to form an electron beam that strikes the anode surface to generate an x-ray beam which passes across the central bore;

a rotatable mounting means for rotatably mounting the cathode around the evacuated interior of the toroidal housing such that a location at which the electron beam strikes the anode surface is rotated to a ring of locations around the annular anode surface;

an x-ray rube mounting means for mounting the toroidal x-ray tube;

a radiation detection means spanning at least an arc for detecting the x-ray beam after it is passed through the imaged subject region in the central bore;

a laser gyro for monitoring an angular position of the cathode;

an image reconstruction means operatively connected with the radiation detection means and the laser gyro for reconstructing an image representation of the image region of the subject.

20. A CT scanner comprising:

a toroidal x-ray tube defining a central bore of sufficient diameter for passage of an imaged region of a subject therethrough, the toroidal x-ray tube including:

a toroidal housing defining an evacuated interior;

an annular anode surface mounted within the toroidal housing interior and extending therearound;

a cathode supporting means movably mounted in the evacuated interior of the toroidal x-ray tube;

a rotating means for rotating the cathode supporting means around the evacuated interior of the toroidal housing;

a cathode means for emitting a beam of electrons which strike the anode surface to generate an x-ray beam that is directed across the central bore, the cathode means being mounted to the cathode supporting means for rotation around the evacuated interior therewith such that the beam of electrons is rotated to strike the anode surface along a ring-shaped path such that the x-ray beam rotates around the central bore;

a vacuum pumping means connected to the toroidal housing evacuated interior for actively maintaining the vacuum therein;

a multiplicity of radiation detectors mounted along at least an arc segment for receiving the x-ray beam after the x-ray beam has traversed the central bore;

a means for monitoring rotating of the cathode supporting means;

an image reconstruction means operatively connected with the radiation detectors and the monitoring means for reconstructing an imaging representation of a region of a subject disposed within the central bore.

21. A CT scanner comprising:

a toroidal x-ray tube housing extending around a central bore and having an evacuated interior;

an annular anode surface mounted within the toroidal housing interior;

a cathode means for emitting electrons to form a beam that strikes the anode surface, the cathode means being mounted on an annular ring within the toroidal housing interior;

a rotating means for rotating the annular ring through the toroidal housing interior around the central bore;

at least one voltage source for applying a sufficient voltage between the cathode means and the anode surface such that the beam of electrons strikes the anode surface with sufficient energy to generate an x-ray beam;

at least one of a compensator and a collimator mounted to the annular ring for rotation therewith and adjacent to the cathode means such that the x-ray beam passes therethrough;

an annular window defined in the toroidal housing through which the x-ray beam exits the housing and is directed toward a central axis of the bore;

a shutter member which is selectively movable into and out of an x-ray blocking relationship with a window;

a multiplicity of radiation detectors mounted along at least an arc segment for receiving the x-ray beam after the x-ray beam has traversed the central bore;

a means for monitoring rotation of the annular ring;

an image reconstruction means operatively connected with the radiation detectors and the rotation monitoring means for reconstructing an image representation of a region of a subject disposed within the central bore.

22. A CT scanner comprising:

a toroidal x-ray tube defining a central bore of sufficient diameter for passage of an imaged region of a subject therethrough, the toroidal x-ray tube including:

a toroidal housing defining an evacuated interior;

an annular anode surface mounted within the toroidal housing interior and extending therearound;

a cathode supporting means movably mounted in the evacuated interior of the toroidal x-ray tube;

a rotating means for rotating the cathode supporting means around the evacuated interior of the toroidal housing;

a cathode means for emitting a beam of electrons which strike the anode surface to generate an x-ray beam that is directed across the central bore, the cathode means being mounted to the cathode supporting means for rotation around the evacuated interior therewith such that the beam of electrons is rotated to strike the anode surface along a ring-shaped path such that the x-ray beam rotates around the central bore;

a collimator mounted to the cathode supporting means and disposed closely adjacent to the anode surface adjacent a location at which the beam of electrons strikes the anode surface such that the x-ray beam passes therethrough and is collimated thereby, the collimator means rotating with the cathode supporting means and the cathode means such that the collimator means rotates with the x-ray beam;

a multiplicity of radiation detectors mounted along at least an arc segment for receiving the x-ray beam after the x-ray beam has traversed the central bore;

a means for monitoring rotating of the cathode supporting means;

an image reconstruction means operatively connected with the radiation detectors and the monitoring means for reconstructing an imaging representation of a region of a subject disposed within the central bore.

23. A CT scanner comprising:

a generally toroidal x-ray tube defining a central bore of sufficient diameter for receiving an imaged region of a subject therein, the x-ray tube including:

a generally toroidal housing held to a substantially neutral potential, the toroidal housing having an evacuated interior;

an anode surface mounted within the toroidal housing interior;

a rotatable ring mounted in the evacuated interior of the toroidal housing, the ring being held substantially to the neutral potential;

at least one cathode cup supported by the rotatable ring, the cathode cup emitting a beam of electrons which strikes the anode surface to generate an x-ray beam which crosses the central bore;

an insulating means for insulating the cathode cup from the rotating ring;

a means for rotating the ring within the evacuated interior of the toroidal housing;

a means for maintaining the cathode cup at a large potential difference relative to the substantially neutral rotating ring, the substantially neutral toroidal housing, and the anode such that the large potential causes the electron beam from the cathode cup to strike the anode with sufficient energy to generate an x-ray beam, which x-ray beam traverses the central bore;

a means for monitoring an angular position of the rotating ring;

an x-ray detection means spanning at least an arc for detecting the x-ray beam after it has traversed the central bore;

an image reconstruction means operatively connected with the radiation means and the position detecting means for reconstructing an image representation of a portion of the subject in the central bore.

* * * * *